United States Patent
Bang et al.

(10) Patent No.: US 11,179,703 B2
(45) Date of Patent: Nov. 23, 2021

(54) CATALYST FOR PROCESSING OXYCHLORINATION OF HYDROCARBON, PREPARATION METHOD THEREFOR, AND PREPARATION METHOD OF OXYCHLORINATED COMPOUND OF HYDROCARBON USING SAME

(71) Applicants: LG CHEM, LTD., Seoul (KR); SEOUL NATIONAL UNIVERSITY R&DB FOUNDATION, Seoul (KR)

(72) Inventors: Jungup Bang, Daejeon (KR); Do Heui Kim, Seoul (KR); Gyo Hyun Hwang, Daejeon (KR); Jongwook Jung, Daejeon (KR); Yongju Bang, Daejeon (KR); Youngseok Ryou, Daejeon (KR); Jeongeun Kim, Gunpo-si (KR)

(73) Assignees: LG CHEM. LTD., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/958,443

(22) PCT Filed: Feb. 22, 2019

(86) PCT No.: PCT/KR2019/002232
§ 371 (c)(1),
(2) Date: Jun. 26, 2020

(87) PCT Pub. No.: WO2019/164342
PCT Pub. Date: Aug. 29, 2019

(65) Prior Publication Data
US 2021/0053036 A1    Feb. 25, 2021

(30) Foreign Application Priority Data
Feb. 23, 2018    (KR) .................. 10-2018-0022215

(51) Int. Cl.
| | |
|---|---|
| *B01J 23/83* | (2006.01) |
| *B01J 23/10* | (2006.01) |
| *B01J 35/02* | (2006.01) |
| *B01J 35/10* | (2006.01) |
| *B01J 37/02* | (2006.01) |
| *B01J 37/08* | (2006.01) |
| *C07C 17/06* | (2006.01) |

(52) U.S. Cl.
CPC .............. *B01J 23/83* (2013.01); *B01J 23/10* (2013.01); *B01J 35/026* (2013.01); *B01J 35/1014* (2013.01); *B01J 35/1019* (2013.01); *B01J 37/0221* (2013.01); *B01J 37/0236* (2013.01); *B01J 37/088* (2013.01); *C07C 17/06* (2013.01)

(58) Field of Classification Search
CPC combination set(s) only.
See application file for complete search history.

(56) References Cited

U.S. PATENT DOCUMENTS

| | | | |
|---|---|---|---|
| 5,113,027 A | 5/1992 | Mainz et al. | |
| 5,334,789 A | 8/1994 | Komatsu et al. | |
| 5,382,726 A | 1/1995 | Young et al. | |
| 5,928,619 A | 7/1999 | Bonneau et al. | |
| 5,986,152 A | 11/1999 | Muller et al. | |
| 9,073,046 B2 * | 7/2015 | Kramer ............... | B01J 35/1019 |
| 2008/0214879 A1 | 9/2008 | Strebelle et al. | |
| 2010/0160697 A1 | 6/2010 | Orsenigo et al. | |
| 2010/0189633 A1 | 7/2010 | Schellen et al. | |
| 2016/0023191 A1 | 1/2016 | Kramer | |

FOREIGN PATENT DOCUMENTS

| | | |
|---|---|---|
| CN | 103721759 A | 4/2014 |
| JP | 6-211525 A | 8/1994 |
| JP | 3092330 B2 | 9/2000 |
| JP | 2010-533059 A | 10/2010 |
| KR | 10-1994-0001934 A | 2/1994 |
| KR | 10-1999-0045511 A | 6/1999 |
| KR | 10-2008-0037900 A | 5/2008 |
| KR | 10-2010-0074017 A | 7/2010 |
| KR | 10-2012-0052062 A | 5/2012 |
| KR | 10-1169626 B1 | 8/2012 |
| KR | 10-2015-0131139 A | 11/2015 |
| KR | 10-2018-0079178 A | 7/2018 |
| WO | WO 95/03877 A1 | 2/1995 |
| WO | WO 2017/216653 A1 | 12/2017 |

OTHER PUBLICATIONS

International Search Report issued in PCT/KR2019/002232 (PCT/ISA/210), dated May 24, 2019.
Scharfe et al., "Mechanism of Ethylene Oxychlorination on Ceria", ACS Catalysis, vol. 8, No. 4, Feb. 15, 2018, pp. 2651-2663.

* cited by examiner

*Primary Examiner* — Jafar F Parsa
(74) *Attorney, Agent, or Firm* — Birch, Stewart, Kolasch & Birch, LLP

(57) ABSTRACT

A catalyst for an oxychlorination process of hydrocarbons, a preparation method thereof, and a method for preparing an oxychlorination compound of hydrocarbons using the same.

15 Claims, 5 Drawing Sheets

[Figure 1]
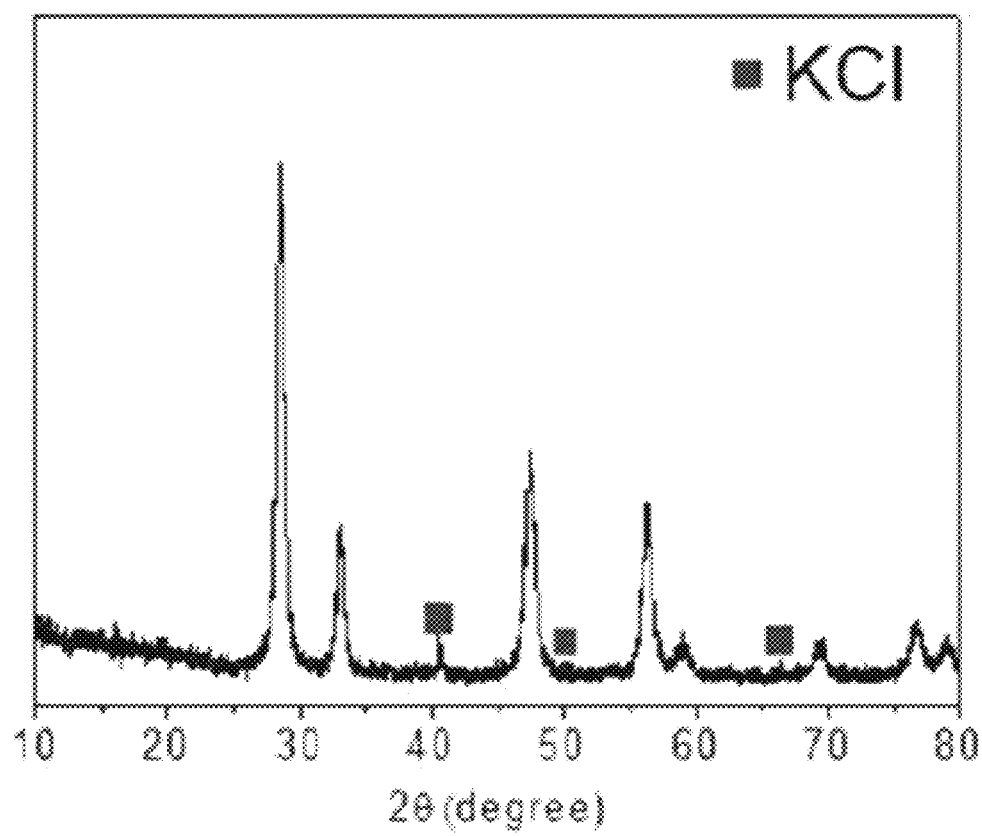

[Figure 2]
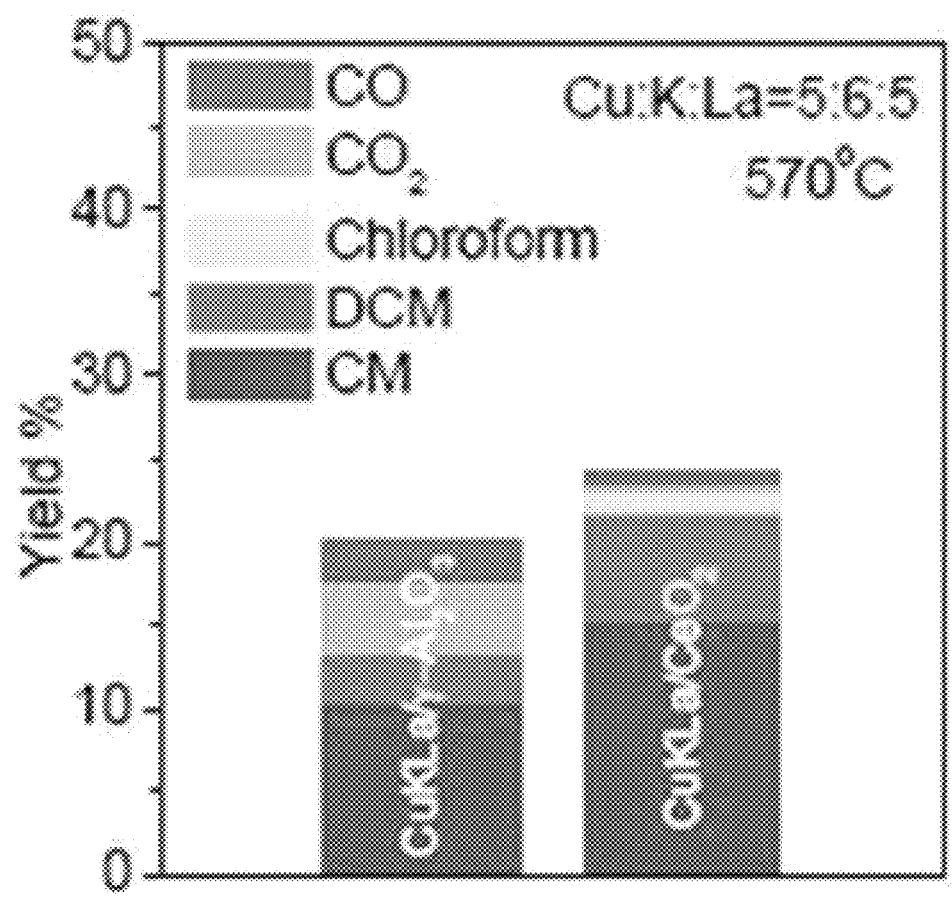

[Figure 3]
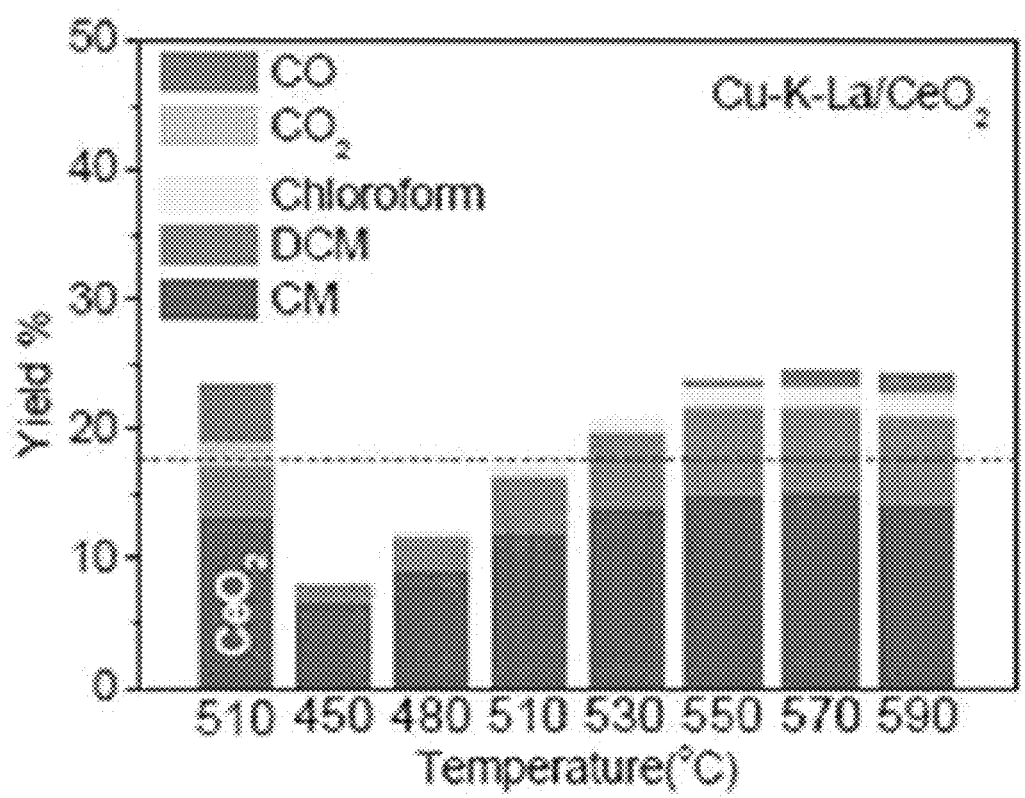

[Figure 4]
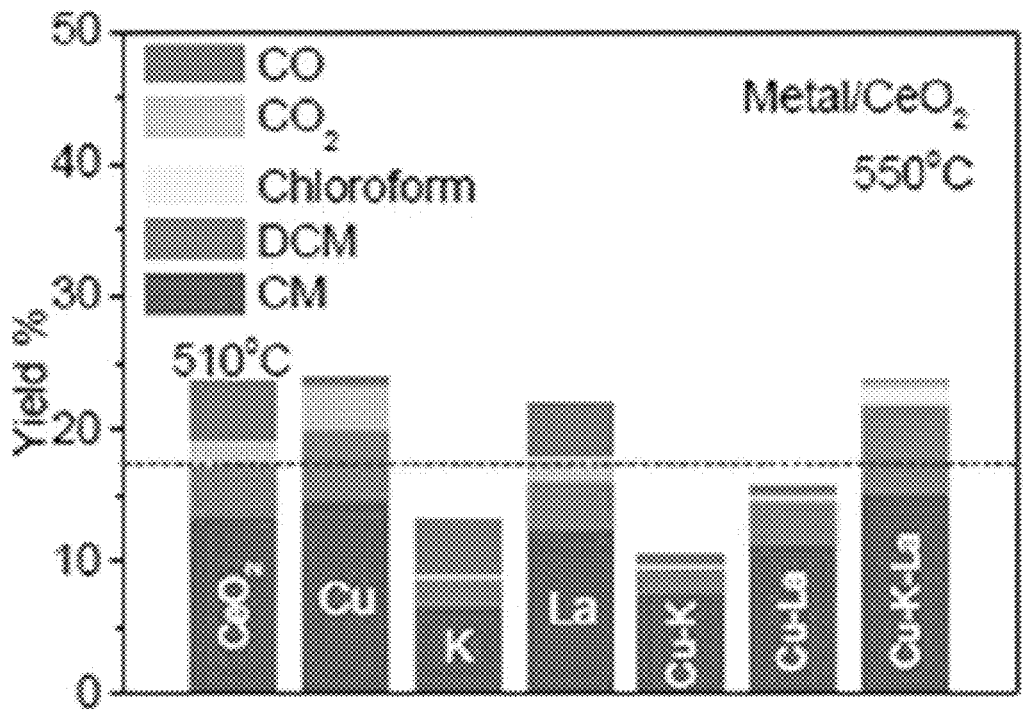
[Figure 5]
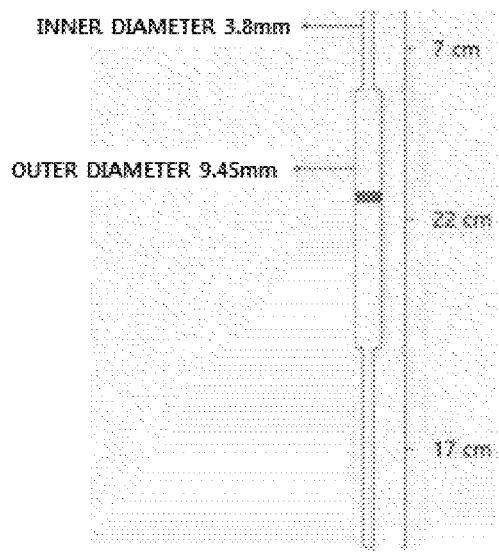

[Figure 6]
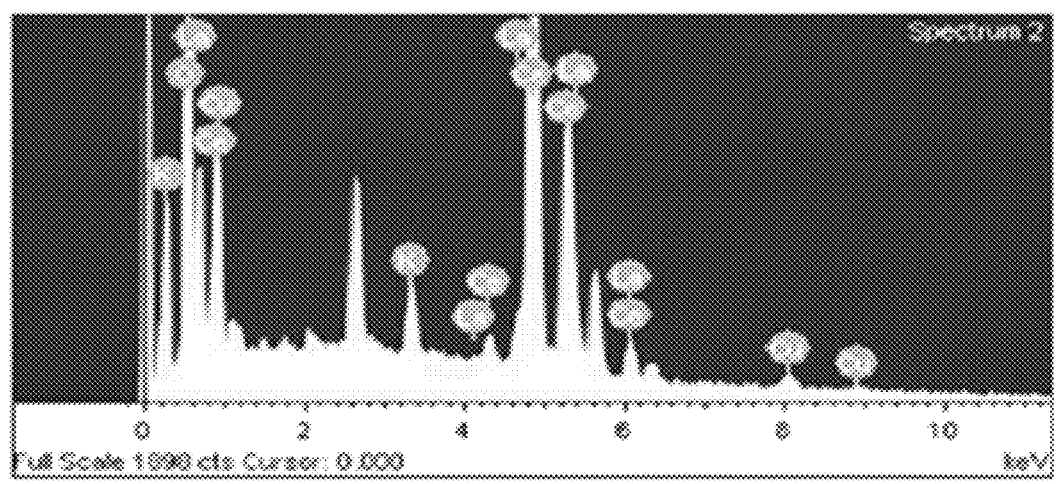

CATALYST FOR PROCESSING OXYCHLORINATION OF HYDROCARBON, PREPARATION METHOD THEREFOR, AND PREPARATION METHOD OF OXYCHLORINATED COMPOUND OF HYDROCARBON USING SAME

TECHNICAL FIELD

This application claims priority to and the benefit of Korean Patent Application No. 10-2018-0022215 filed in the Korean Intellectual Property Office on Feb. 23, 2018, the entire contents of which are incorporated herein by reference.

The present specification relates to a catalyst for an oxychlorination process of hydrocarbons, a preparation method thereof, and a method for preparing an oxychlorination compound of hydrocarbons using the same.

BACKGROUND ART

The importance on studies on the method of utilizing natural gas which is cheap and rich in reserves due to the continuous increase in oil prices has further increased, and the prior arts concerning pyrolysis reactions of methane in natural gas using oxygen and coupling reactions of methane in natural gas using a catalyst have been mainly reported. Further, as a method in the related art that may use a chlorine compound for the activation of methane, methods of pyrolyzing methane and chlorine at high temperature are disclosed in U.S. Pat. Nos. 4,199,533, 4,804,797, 4,714,796 and 4,983,783, and the like. However, since the high temperature pyrolysis of methane by chlorine depends on the amount of heat supplied and the reaction time, which are simply provided, in the control of selectivity, lots of byproducts such as methylene chloride or cokes are additionally generated.

PRIOR ART DOCUMENT

[Patent Document]
Korean Patent Application Laid-Open No. 10-2010-0074017

DETAILED DESCRIPTION OF INVENTION

Technical Problem

The present specification provides a catalyst for an oxychlorination process of hydrocarbons, a preparation method thereof, and a method for preparing an oxychlorination compound of hydrocarbons using the same.

Technical Solution

An exemplary embodiment of the present specification provides a catalyst for an oxychlorination process of hydrocarbons, the catalyst including: a catalyst material including copper; and a carrier including cerium oxide ($CeO_2$), in which the catalyst material further includes one or more first co-catalysts selected from the group consisting of an alkali metal and an alkaline earth metal; and a second co-catalyst including a lanthanide metal.

Further, an exemplary embodiment of the present specification provides a method for preparing the catalyst for an oxychlorination process of hydrocarbons, the method including: preparing a carrier including cerium oxide ($CeO_2$); and supporting a catalyst material including copper, a first co-catalyst, and a second co-catalyst on the carrier.

In addition, an exemplary embodiment of the present specification provides a method for preparing an oxychlorination compound of hydrocarbons, which is performed in the presence of the catalyst for an oxychlorination process of hydrocarbons and includes an oxychlorination reaction of hydrocarbons.

Advantageous Effects

The catalyst for an oxychlorination process of hydrocarbons according to the present specification has an effect in that it is possible to increase the selectivity of a target product when used for an oxychlorination process.

Further, the catalyst for an oxychlorination process of hydrocarbons according to the present specification has an effect in that it is possible to suppress the production of byproducts such as carbon monoxide or carbon dioxide when used for an oxychlorination process.

In addition, the catalyst for an oxychlorination process of hydrocarbons according to the present specification has an effect in that it is possible to increase the selectivity of a target product even at low temperature when used for an oxychlorination process.

BRIEF DESCRIPTION OF DRAWINGS

FIG. 1 illustrates an XRD pattern of a catalyst according to Example 1.

FIGS. 2 to 4 illustrate results of Experimental Example 1 or Experimental Example 2.

FIG. 5 illustrates a reactor used in a process test.

FIG. 6 illustrates the EDS data of a catalyst of Example 2.

BEST MODE

Hereinafter, the present specification will be described.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

In the present specification, the "catalyst material" may be an "active material" having catalytic activity.

In the present specification, unless otherwise mentioned, the "catalyst" may be a catalyst for an oxychlorination process of hydrocarbons.

In the present specification, the "oxychlorination process of hydrocarbons" may mean a process for substituting hydrogen of hydrocarbons with chlorine, and may also be named an oxidative chlorination process of hydrocarbons. For example, the oxychlorination process of hydrocarbons may be a process of producing a chloromethane ($CH_3Cl$, $CH_2Cl_2$, or $CHCl_3$) by substituting hydrogen of a methane gas ($CH_4$) with chlorine, and may be represented by the following Formula (I). The chloromethane produced through the following General Formula (I) may be converted into a useful chemical product through the following General Formula (II). In the following General Formula (I), not only a chloromethane, but also a byproduct such as carbon monoxide or carbon dioxide may be produced.

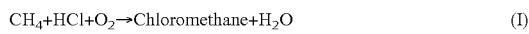

$$CH_4 + HCl + O_2 \rightarrow Chloromethane + H_2O \quad (I)$$

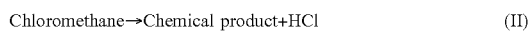

$$Chloromethane \rightarrow Chemical\ product + HCl \quad (II)$$

The present specification has been made in an effort to provide a catalyst which is used for the process of General Formula (I) and may minimize the selectivity of byproducts while increasing the selectivity of chloromethane in a product.

The present specification provides a catalyst for an oxychlorination process of hydrocarbons, the catalyst including: a catalyst material including copper; and a carrier including cerium oxide ($CeO_2$), in which the catalyst material further includes one or more first co-catalysts selected from the group consisting of an alkali metal and an alkaline earth metal; and a second co-catalyst including a lanthanide metal. As the carrier includes cerium oxide, it is possible to induce effects of enhancing catalytic stability and increasing the service life and the production amount by excellent oxygen adsorption-desorption performance of cerium oxide. Further, as a cerium oxide carrier includes both the copper and the co-catalysts, the above-described effects may be enhanced.

The present specification may be used in a packed bed, fluidized bed, or circulating fluidized bed reactor by including cerium oxide as a carrier, using copper as an active material included in a catalyst material, and using the above-described first co-catalyst and second co-catalyst in the preparation of a chloro compound through an oxychlorination reaction of hydrocarbons.

Further, the present specification has been made in an effort to maximally suppress the production of byproducts generated during the oxychlorination process of hydrocarbons and maximize the production of a target product by using the catalyst according to an exemplary embodiment of the present specification. For example, when a reactant is methane ($CH_4$) and the target products are $CH_3Cl$, $CH_2Cl_2$, and $CHCl_3$ which are chlorination compounds of methane, $CO_2$ and $CO$ as byproducts are generated, and in this case, the present specification has been made in an effort to maximize the amount of chlorination methanes $CH_3Cl$, $CH_2Cl_2$, and $CHCl_3$ produced and minimize the generation of $CO_2$ and $CO$ as byproducts. In this case, the present specification has been made in an effort to induce the reduction in process costs by increasing the amount of target product produced while suppressing a risk that may occur due to the process by minimizing the amount of harmful materials carbon dioxide and carbon monoxide generated.

In an exemplary embodiment of the present specification, the catalyst for an oxychlorination process of hydrocarbons may be a catalyst in which copper, one or more first co-catalysts selected from the group consisting of an alkali metal and an alkaline earth metal, and a second co-catalyst including a lanthanide metal are supported on the carrier including cerium oxide ($CeO_2$). The supporting method is not particularly limited as long as the method is generally used in the art to which the technology pertains, and a specific method thereof will be described below.

In an exemplary embodiment of the present specification, copper included in the catalyst material may be used as an active material. Specifically, copper is included in a catalyst material, so that there is an effect in that it is possible to reduce the selectivity of byproducts such as carbon monoxide or carbon dioxide which may be generated during the oxychlorination process of hydrocarbons.

In an exemplary embodiment of the present specification, the catalyst material may further include platinum (Pt), palladium (Pd), nickel (Ni), cobalt (Co), ruthenium (Ru), rhenium (Re), rhodium (Rh), osmium (Os), titanium (Ti), vanadium (V), chromium (Cr), manganese (Mn), iron (Fe), or zinc (Zn) as the active material, in addition to copper, and these elements may be used either alone or in the form of an alloy.

In an exemplary embodiment of the present specification, the catalyst material may be supported on the carrier. The method of supporting the catalyst material is not particularly limited as long as the method is generally used in the art to which the technology pertains, and a specific method thereof will be described below.

In an exemplary embodiment of the present specification, the catalyst material may be included in an amount of 5 wt % to 25 wt %, preferably 10 wt % to 23 wt %, and more preferably 15 wt % to 20 wt %, based on the total weight of the catalyst for an oxychlorination process of hydrocarbons. When the content of the catalyst material satisfies the numerical range, the function of the catalyst by the catalyst material may be efficiently performed, and there is an effect in that it is possible to suppress the non-activation phenomenon of the catalyst.

In an exemplary embodiment of the present specification, the contents of the first co-catalyst and the second co-catalyst are the same as or different from each other, and may be each 10 parts by weight to 2,000 parts by weight, 15 parts by weight to 1,000 parts by weight, 20 parts by weight to 500 parts by weight, 80 parts by weight to 300 parts by weight, or 100 parts by weight to 200 parts by weight, based on 100 parts by weight of copper. When the contents of the first co-catalyst and the second co-catalyst satisfy the numerical range, the reaction active point of the catalyst may be increased. The content of the catalyst material (or the first co-catalyst and the second co-catalyst) means the degree to which the catalyst material (or the first co-catalyst and the second co-catalyst) is supported on a carrier.

In an exemplary embodiment of the present specification, the first co-catalyst may include one or more selected from the group consisting of sodium, lithium, potassium, magnesium, and calcium.

In an exemplary embodiment of the present specification, the first co-catalyst may include potassium. When potassium is included as the first co-catalyst, there is an effect in that the contribution to the active material may be increased.

In an exemplary embodiment of the present specification, the second co-catalyst may include one or more selected from the group consisting of yttria and a rare earth element.

In an exemplary embodiment of the present specification, the rare earth element may be scandium (Sc), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or lutetium (Lu).

In an exemplary embodiment of the present specification, the second co-catalyst may include lanthanum. When lanthanum is included as the second co-catalyst, there is an effect in that the contribution to the active material may be increased.

In an exemplary embodiment of the present specification, the first co-catalyst may be potassium and the second co-catalyst may be lanthanum. In this case, the contribution to the active material may be maximized.

In an exemplary embodiment of the present specification, the carrier may have a cerium oxide ($CeO_2$) single composition. The cerium oxide ($CeO_2$) single composition means that the carrier rarely includes materials other than cerium oxide, or includes a small amount of materials other than cerium oxide even though the carrier includes the materials. For example, the content of cerium oxide may be 80 wt % or more, 90 wt % or more, 95 wt % or more, or 99 wt % or more, and most preferably 100 wt %, based on the total 100 weight of the carrier.

It is possible to confirm, by a general method used in the art to which the technology pertains, that the carrier has a cerium oxide ($CeO_2$) single composition. For example, it is possible to confirm the presence or absence of $CeO_2$ by confirming X-ray diffraction peak patterns. Specifically, when peaks corresponding to (111), (200), (220), and (311) crystal planes are present, it is possible to confirm that $CeO_2$ on the cubic is present. Further, it is possible to confirm the presence or absence and wt % of Ce and O atoms by the energy dispersive spectroscopy (EDS) measurement. The EDS analysis is used to confirm the chemical composition of a sample along with SEM photographs. During the EDS measurement on cerium oxide, peaks corresponding to Ce and O atoms are observed. In contrast, when a peak of an atom other than Ce and O atoms is rarely observed, it is possible to confirm that the carrier has a cerium oxide single composition.

In an exemplary embodiment of the present specification, the carrier may be composed of only cerium oxide.

In an exemplary embodiment of the present specification, the carrier including cerium oxide ($CeO_2$) may be in the form of a powder, the powder may be in the form of a sphere, and the diameter of a catalyst including the carrier will be described below.

In an exemplary embodiment of the present specification, an "A-B-C/$CeO_2$ catalyst" may mean that A, B, and C as a metal or metal oxide are supported on a $CeO_2$ carrier.

In an exemplary embodiment of the present specification, the carrier may have a specific surface area of 50 $m^2$/g to 250 $m^2$/g, 100 $m^2$/g to 200 $m^2$/g, and preferably 130 $m^2$/g to 150 $m^2$/g. When the specific surface area of the carries satisfies the numerical range, the contact area with an active component of the catalyst may be widely secured, and when an inlet gas is delivered into the catalyst, the material delivery resistance is appropriately controlled, so that the excellent conversion of the raw material gas may be achieved. The specific surface area of the carrier may mean the area ($m^2$) of pores in the carrier based on the total weight (g) of the carrier. The specific surface area of the carrier may be measured by a method generally used in the art, and may be measured, for example, by the Brunauer, Emmett and Teller (BET) method. The method is a type of a vapor adsorption method that adsorbs molecules or ions onto the surface of a carrier and measures the surface area from the amount of molecules or ions adsorbed, and after a sample is stored at 250° C. for 5 hours, the specific surface area may be measured by using an $N_2$ adsorption-desorption isotherm using the Micromeritics ASAP 2010 apparatus.

In an exemplary embodiment of the present specification, the carrier may further include a composite oxide including one or more elements selected from the group consisting of Zr, Y, an alkali metal element, an alkaline earth metal element, a lanthanide element, and a rare earth element. Specific examples on the alkali metal element, the alkaline earth metal element, the lanthanide element, and the rare earth element are the same as those described above.

In an exemplary embodiment of the present specification, examples of the composite oxide include a CeZr composite oxide (70:30), a CeZrLa composite oxide (86:10:4), a CeZrLa composite oxide (66:29:5), a CeZrLaY composite oxide (40:50:5:5), a CeZrPr composite oxide (40:55:5), a CeZrLaNdPr composite oxide, a CeZrNdPrCa composite oxide, or the like. The numbers in the parenthesis in the latter part mean the ratios of the weights of respective elements.

In an exemplary embodiment of the present specification, the catalyst for an oxychlorination process of hydrocarbons may have a diameter of 0.1 mm to 1.0 mm, preferably 0.1 mm to 0.5 mm, and more preferably 0.18 mm to 0.25 mm. When the catalyst diameter is less than 0.1 mm, a pressure drop phenomenon in a reactor significantly occurs, so that the conversion or reaction rate may deteriorate. In contrast, when the catalyst diameter is more than 1.0 mm, a channeling phenomenon in which a reactant does not go through a catalyst layer may occur. The diameter of the catalyst may mean an average particle diameter of catalyst particles. The diameter of the catalyst may be measured by a method generally used in the art, and for example, diameters of two or more catalyst particles may be measured by using scanning electron microscopy (SEM) or transmission electron microscopy (TEM), and an average of the measured diameters of the particles may be calculated as an average particle diameter.

An exemplary embodiment of the present specification provides a method for preparing the above-described catalyst for an oxychlorination process of hydrocarbons, the method including: preparing a carrier including cerium oxide ($CeO_2$); and supporting an active material including copper, a first co-catalyst, and a second co-catalyst on the carrier.

In an exemplary embodiment of the present specification, the supporting of the active material including copper, the first co-catalyst, and the second co-catalyst on the carrier may use an incipient wetness method and may also use other wetness methods. As the precipitation method, a coprecipitation method, a homogeneous precipitation method, a sequential precipitation method, or the like may be used. When a catalyst powder is prepared by the precipitation method, a catalyst in a powder state may be obtained and the proportion of the active material may be freely adjusted by simultaneously precipitating an active material and a carrier as constituent elements, and a catalyst powder which is excellent in stability may be prepared by strengthening the mutual bonding strength between the active material and the carrier.

In an exemplary embodiment of the present specification, the supporting of the active material including copper; the first co-catalyst; and the second co-catalyst on the carrier may be performed by a method of putting the carrier into an aqueous precursor solution including: an active material precursor including an active material precursor; a first co-catalyst precursor including a first co-catalyst; and a second co-catalyst precursor including a second co-catalyst, and stirring the resulting mixture.

In an exemplary embodiment of the present specification, the active material precursor, the first co-catalyst precursor, and the second co-catalyst precursor may vary depending on the type of target material. For example, when the active material is copper, the active material precursor may be copper chloride dihydrate ($CuCl_2.2H_2O$), and when the first co-catalyst material is potassium, the first co-catalyst precursor may be potassium chloride (KCl), and when the second co-catalyst is lanthanum, the second co-catalyst precursor may be lanthanum chloride heptahydrate ($LaCl_3.7H_2O$).

In an exemplary embodiment of the present specification, the stirring may be performed such that the aqueous precursor solution may be supported on the carrier well, and may be performed for 0.5 hour or more, preferably, 1 hour or more.

In an exemplary embodiment of the present specification, the method for preparing a catalyst for an oxychlorination process of hydrocarbons may include: drying a catalyst; and calcining the catalyst.

In an exemplary embodiment of the present specification, the drying of the catalyst is for evaporating moisture of the catalyst, and the method of drying the catalyst is not particularly limited as long as the method is generally used in the art to which the technology pertains. For example, the drying of the catalyst may be performed by a method of evaporating moisture using a rotary evaporator and drying the catalyst at a temperature of 100° C. for 10 hours or more.

In an exemplary embodiment of the present specification, the calcining of the catalyst is performed to remove a precursor material remaining in the catalyst after the supporting of the catalyst material, and a method of calcining the catalyst is not particularly limited as long as the method is generally used in the art to which the technology pertains, and may be performed at a temperature of 400° C. or more for 1 to 10 hours, for example. When the performance temperature and the performance time are satisfied, it is possible to effectively remove the precursor material, and to suppress a problem with deterioration in durability caused by the occurrence of phase change in carrier.

An exemplary embodiment of the present specification provides a method for preparing an oxychlorination compound of hydrocarbons, which is performed in the presence of the above-described catalyst for an oxychlorination process of hydrocarbons and includes an oxychlorination reaction of hydrocarbons. When the above-described catalyst for an oxychlorination process of hydrocarbons is applied, an amount of oxychlorination compound of hydrocarbons produced is increased and the reduction in activity of the catalyst is low. That is, the above-described catalyst for an oxychlorination process of hydrocarbons exhibits excellent activity even at low temperature, and thus has an advantage in that the catalyst is suitable for a low-temperature process.

In an exemplary embodiment of the present specification, the method for preparing an oxychlorination compound of hydrocarbons may be expressed as a 'process' in the present specification.

In an exemplary embodiment of the present specification, the fact that the method is performed in the presence of a catalyst for an oxychlorination process of hydrocarbons may mean inducing a reaction by allowing a reaction gas and the like to flow into a reactor in which a catalyst for an oxychlorination process of hydrocarbons is mounted.

In an exemplary embodiment of the present specification, the oxychlorination reaction of hydrocarbons means a reaction of substituting hydrogen of a hydrocarbon raw material gas with chlorine, and is the same as described above.

In an exemplary embodiment of the present specification, an inlet gas means a collection of gases flowing into a reactor, and is differentiated from an outlet gas discharged outside the reactor after the reaction.

In an exemplary embodiment of the present specification, the method for preparing an oxychlorination compound of hydrocarbons may be performed by bringing an inlet gas into contact with the above-described catalyst. A partial oxidation reaction of the hydrocarbons is performed by bringing an inlet gas including a hydrocarbon raw material gas and a hydrogen chloride gas into contact with a catalyst. The meaning of the contact may be explained by a catalyst theory. Specifically, a catalyst includes a certain active site or active center, and a catalytic action is performed at the active site or active center. While the inlet gas is brought into contact with the active site or active center, the catalytic reaction occurs. For example, there is a method of loading a catalyst into a reactor and circulating the inlet gas in the reactor.

In an exemplary embodiment of the present specification, the inlet gas may include a hydrocarbon raw material gas, a hydrogen chloride gas, and an oxygen gas.

In an exemplary embodiment of the present specification, the hydrocarbon raw material gas is a gas including carbon and hydrogen, and means a gas which is a raw material for a target product. Examples thereof include: a straight-chained or branched saturated aliphatic hydrocarbon having 1 to 16 carbon atoms, such as methane, ethane, propane, butane, pentane, hexane, heptane, octane, nonane, and decane; an alicyclic saturated hydrocarbon, such as cyclohexane, methylcyclohexane, and cyclooctane; a monocyclic or polycyclic aromatic hydrocarbon; urban gas; LPG; naphtha; and a hydrocarbon such as kerosene.

In an exemplary embodiment of the present specification, the hydrogen chloride gas (HCl) may function as a supply source of chlorine atoms.

In an exemplary embodiment of the present specification, the inlet gas may further include one or two or more inert gases selected from the group consisting of nitrogen, helium, argon, and carbon dioxide.

In an exemplary embodiment of the present specification, the ratio of the volume flow rates of the hydrocarbon raw material gas to the hydrogen chloride gas may be 1:1 to 10:1, preferably 1:1 to 5:1, more preferably 1:1 to 3:1, and most preferably 1.5:1 to 2.5:1. When the ratio satisfies the numerical range, the excellent activity of the catalyst may be maintained. Accordingly, there is an advantage in that the selectivity of the target product may be maintained at a high level.

In an exemplary embodiment of the present specification, the inlet gas may further include an oxygen gas, and the ratio of the volume flow rates of the hydrocarbon raw material gas to the oxygen gas may be 1:1 to 10:1, preferably 2:1 to 6:1, and more preferably 3:1 to 5:1. When the ratio of the volume flow rates of the hydrocarbon raw material gas to the oxygen gas is less than 1:1, the selectivity of chloromethane as the target product may be decreased, and when the ratio of the volume flow rates of the hydrocarbon raw material gas to the oxygen gas is more than 10:1, there may be a problem in that the selectivity of byproducts such as carbon monoxide or carbon dioxide is increased.

In an exemplary embodiment of the present specification, the ratio of the volume flow rates of the hydrocarbon raw material gas to the inert gas may be 1:0.5 to 1:10, preferably 1:0.5 to 1:5.

The ratio of the volume flow rates may be measured by a method generally used in the art to which the technology pertains, and may be achieved by adjusting the temperature and pressure of an inlet gas flowing into a reactor. For example, the ratio of the volume flow rates may be measured at room temperature (25° C.) and normal pressure (1 atm), and may be measured by using a volumetric flow meter generally used in the art.

In an exemplary embodiment of the present specification, the process may be performed under a process temperature of 450° C. to 550° C., a pressure of 0.5 atm to 3 atm, and a space velocity of 2,000 $h^{-1}$ to 20,000 $h^{-1}$.

In an exemplary embodiment of the present specification, the process may be performed under a process temperature of 450° C. to 530° C., 450° C. or more and less than 530°

C., 450° C. to 520° C., or 450° C. to 510° C. When the process temperature satisfies the range, it is possible to suppress byproducts from being produced and to increase the selectivity of a target product. For example, when the hydrocarbon raw material is methane, the process proceeds in the order of 1) the production of a Cl activated species through oxidation of hydrogen chloride, 2) the production of $CH_3Cl$ through reaction of methane and the Cl activated species, and 3) the production of byproducts such as carbon monoxide or carbon dioxide from the additional reaction of produced $CH_3Cl$ or the oxidation of methane. In this case, when the process temperature is low, the effect of the catalyst on the reaction is predominant, so that the rate of producing the Cl activated species in the reaction of 1) becomes faster than the rate of consuming the Cl activated species in the reaction of 2) through the oxidation-reduction ability of the catalyst itself. However, when the process temperature is high, the rate of the reaction of 3) becomes faster while the effect of temperature is gradually increased, so that there is a problem in that the production of byproducts is increased.

The present specification intends to suppress byproducts such as carbon monoxide or carbon dioxide from being produced by appropriately maintaining the rates of the reactions of 1) and 2) while controlling the rate of the above-described reaction of 3) by adjusting the process conditions as described above.

In an exemplary embodiment of the present specification, the rate at which the inlet gas is flowing may be 10,000 ml/(h·gcat) to 50,000 ml/(h·gcat). When the rate satisfies the range, the inlet gas is sufficiently fluid, so that it is possible to effectively suppress cokes from being generated. The gcat means the content of catalyst loaded into a reactor.

In an exemplary embodiment of the present specification, the method for preparing an oxychlorination compound of hydrocarbons may be performed in a packed bed reactor, a fluidized bed reactor, or a circulating fluidized bed reactor.

In an exemplary embodiment of the present specification, the method for preparing an oxychlorination compound of hydrocarbons may further include a neutralization process. The neutralization process is a process for removing a hydrogen chloride gas included in a reactant. Specifically, the neutralization process may be performed by allowing the reactant to pass through a reactor loaded with a sodium carbonate bed. The neutralization process may produce 1 equivalent of a carbon dioxide gas and 2 equivalents of sodium chloride by allowing 1 equivalent of sodium carbonate and 2 equivalents of hydrogen chloride to react, and may be expressed by the following drawing.

$$Na_2CO_3(s) + 2HCl(g) \rightarrow 2NaCl(aq) + H_2O(l) + CO_2(g)$$

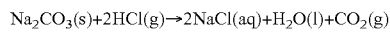

MODE FOR INVENTION

Hereinafter, the above-described contents will be described through Examples. However, the right scope of the present specification is not limited by the following Examples.

Example 1

A cerium oxide carrier ($CeO_2$) powder (3 g, from Rhodia®, surface area: 130 m²/g or more) was prepared as a carrier. Copper (Cu), potassium (K), and lanthanum (La) as catalyst materials were supported on the $CeO_2$ carrier by the following method. In this case, a copper chloride dihydrate ($CuCl_2 \cdot 2H_2O$) was used as a copper (Cu) precursor. Potassium chloride (KCl) was used as a potassium (K) precursor. Lanthanum chloride heptahydrate ($LaCl_3 \cdot 7H_2O$) was used as a lanthanum (La) precursor.

A precursor solution was prepared by weighing the calculated amounts of the precursors and dissolving the precursors in distilled water, the cerium oxide carrier was produced in a powder state and then put into the precursor solution and stirred sufficiently for 1 hour, and then the catalyst materials were supported on the cerium oxide carrier by evaporating water using a rotary evaporator. Thereafter, a catalyst was prepared by drying the carrier at a temperature of 100° C. for about 12 hours or more, and then firing the dried carrier at a temperature of 600° C. for 6 hours.

In this case, the ratio of the weights of copper, potassium, and lanthanum supported on the catalyst was maintained at a weight ratio of Cu:K:La=5:6:5, the contents of the components in the catalyst were 5 wt %, 6 wt %, and 5 wt %, respectively, based on the total weight of the catalyst (total sum of the weights of the carrier and the catalyst materials).

FIG. 1 is a view according to the X-ray diffraction (XRD) of the catalyst according to Example 1. The X-ray diffraction analysis may be measured under the measurement conditions of 40 kV and 30 mA by using the Ultra X18 (Rigaku Corp.). Cu K-alpha may be used as a radiation source, and the X-ray diffraction analysis was measured at a scanning step of 0.02°.

Example 2

A catalyst was prepared in the same manner as in Example 1, except that the ratio of weights of copper, potassium, and lanthanum as catalyst materials was adjusted to a weight ratio of Cu:K:La=7:2:2. In this case, the ratio of the weights of copper, potassium, and lanthanum supported on the catalyst was maintained at a weight ratio of Cu:K:La=7:2:2, the contents of the components in the catalyst were 7 wt %, 2 wt %, and 2 wt %, respectively, based on the total weight of the catalyst (total sum of the weights of the carrier and the catalyst materials).

The EDS confirmation data of the catalyst in Example 2 are illustrated in FIG. 6. Through the EDS confirmation data, it could be confirmed that Cu, K, and La were supported on the catalyst, and particularly, a $CeO_2$ carrier including Ce and O elements was used. In particular, through the fact that elements other than the elements of the catalyst materials and $CeO_2$ were not confirmed, it could be confirmed that the catalyst had a cerium oxide ($CeO_2$) single composition.

Comparative Example 1

A γ-$Al_2O_3$ powder (3 g, from Sasol Co. surface area: 192 m²/g) was prepared as a carrier. Copper (Cu), potassium (K), and lanthanum (La) as catalyst materials were supported on the γ-$Al_2O_3$ carrier by the following method. In this case, a copper chloride dihydrate ($CuCl_2 \cdot 2H_2O$) was used as a copper (Cu) precursor. Potassium chloride (KCl) was used as a potassium (K) precursor. Lanthanum chloride heptahydrate ($LaCl_3 \cdot 7H_2O$) was used as a lanthanum (La) precursor.

A precursor solution was prepared by weighing the calculated amounts of the precursors and dissolving the precursors in distilled water, the γ-$Al_2O_3$ carrier was produced in a powder state and then put into the precursor solution and stirred sufficiently for 1 hour, and then the catalyst materials were supported on the cerium oxide carrier by evaporating water using a rotary evaporator. Thereafter, a catalyst was prepared by drying the carrier at a temperature of 120° C. for about 12 hours, and then firing the dried carrier at a temperature of 550° C. for 4 hours.

In this case, the ratio of copper, potassium, and lanthanum on the catalyst was maintained at a weight ratio of Cu:K:La=5:6:5, the contents of the components in the catalyst were 5 wt %, 6 wt %, and 5 wt %, respectively, based on the total weight of the catalyst (total sum of the weights of the carrier and the catalyst materials).

Comparative Example 2

A γ-$Al_2O_3$ powder (3 g, from Sasol Co. surface area: 192 $m^2$/g) was prepared as a carrier. Copper (Cu), potassium (K), and lanthanum (La) as catalyst materials were supported on the γ-$Al_2O_3$ carrier by the following method. In this case, a copper chloride dihydrate ($CuCl_2.2H_2O$) was used as a copper (Cu) precursor. Potassium chloride (KCl) was used as a potassium (K) precursor. Lanthanum chloride heptahydrate ($LaCl_3.7H_2O$) was used as a lanthanum (La) precursor.

A precursor solution was prepared by weighing the calculated amounts of the precursors and dissolving the precursors in distilled water, the γ-$Al_2O_3$ carrier was produced in a powder state and then put into the precursor solution and stirred sufficiently for 1 hour, and then the catalyst materials were supported on the cerium oxide carrier by evaporating water using a rotary evaporator. Thereafter, a catalyst was prepared by drying the carrier at a temperature of 100° C. for about 12 hours, and then firing the dried carrier at a temperature of 600° C. for 4 hours.

In this case, the ratio of copper, potassium, and lanthanum on the catalyst was maintained at a weight ratio of Cu:K:La=7:2:2, the contents of the components in the catalyst were 7 wt %, 2 wt %, and 2 wt %, respectively, based on the total weight of the catalyst (total sum of the weights of the carrier and the catalyst materials).

Comparative Example 3

A CeZr powder (3 g, from Sasol Co., surface area: 192 $m^2$/g) was prepared as a carrier. Copper, potassium, and lanthanum were supported on the catalyst in the same manner as in Comparative Example 1, the contents of the components in the catalyst were 7 wt %, 2 wt %, and 2 wt %, respectively, based on the total weight of the catalyst (total sum of the weights of the carrier and the catalyst materials), and the weight ratio of Ce:Zr of the carrier was 7:3.

Comparative Example 4

A catalyst was prepared in the same manner as in Example 1, except that no other metals were supported. In this case, as the cerium oxide carrier ($CeO_2$) powder, the powder which is the same as that described in Example 1 was used.

Comparative Example 5

A catalyst was prepared in the same manner as in Example 1, except that only copper was supported on the cerium oxide carrier. In this case, as the precursor solution of copper and the cerium oxide carrier ($CeO_2$) powder, the precursor solution and the cerium oxide carrier ($CeO_2$) powder which are the same as those described in Example 1 were used.

Comparative Example 6

A catalyst was prepared in the same manner as in Example 1, except that only potassium (K) was supported on the cerium oxide carrier. In this case, as the precursor solution of potassium and the cerium oxide carrier ($CeO_2$) powder, the precursor solution and the cerium oxide carrier ($CeO_2$) powder which are the same as those described in Example 1 were used.

Comparative Example 7

A catalyst was prepared in the same manner as in Example 1, except that only lanthanum (La) was supported on the cerium oxide carrier. In this case, as the precursor solution of lanthanum and the cerium oxide carrier ($CeO_2$) powder, the precursor solution and the cerium oxide carrier ($CeO_2$) powder which are the same as those described in Example 1 were used.

Comparative Example 8

A catalyst was prepared in the same manner as in Example 1, except that only copper (Cu) and potassium (K) were supported on the cerium oxide carrier. In this case, as the precursor solutions of copper and potassium and the cerium oxide carrier ($CeO_2$) powder, the precursor solutions and the cerium oxide carrier ($CeO_2$) powder which are the same as those described in Example 1 were used.

Comparative Example 9

A catalyst was prepared in the same manner as in Example 1, except that only copper (Cu) and lanthanum (La) were supported on the cerium oxide carrier. In this case, as the precursor solutions of copper and lanthanum and the cerium oxide carrier ($CeO_2$) powder, the precursor solutions and the cerium oxide carrier ($CeO_2$) powder which are the same as those described in Example 1 were used.

Comparative Example 10

A cerium oxide carrier ($CeO_2$) powder (3 g, from Rhodia®, surface area: 130 $m^2$/g or more) was prepared as a carrier. Iron (Fe), potassium (K), and lanthanum (La) as catalyst materials were supported on the $CeO_2$ carrier by the following method.

In this case, iron (III) nitrate nonahydrate was used as a precursor of iron. The precursors of the other K and La, the supporting conditions, and the drying and firing conditions were the same as those in Example 1.

In this case, the ratio of the weights of iron, potassium, and lanthanum supported on the catalyst was maintained at a weight ratio of Fe:K:La=5:6:5, the contents of the components in the catalyst were 5 wt %, 6 wt %, and 5 wt %, respectively, based on the total weight of the catalyst (total sum of the weights of the carrier and the catalyst materials).

<Experiment on Oxychlorination Reaction of Methane>

Experiment Condition

The particle sizes of the catalysts prepared in the Examples and the Comparative Examples were adjusted by sieving to 180 μm to 250 μm.

A packed bed reactor (PBR) formed of a quartz material as illustrated in FIG. 5 was applied to the experiment. The portion indicated with a blue color in the drawing was loaded with the catalysts according to the Examples and the Comparative Examples. The process temperature was adjusted by using a thermocouple provided outside the packed bed reactor.

The composition of the inlet gas was composed of a volume ratio of $CH_4:O_2:HCl:Ar:N_2=4:1:2:3:10$, and the volume flow rate of the inlet gas and the ratio $[F_T/W_{cat}]$ of flow rate/catalyst weight were adjusted to 50 ml/min and 30,000 ml/(h·$g_{cat}$) respectively, by adjusting the pressure in the reactor. The $CH_4:O_2:HCl$ are reactant gases, and the Ar acts as a diluent.

After all the gas conditions were completely set, an experiment was started after the reactor was pre-heated up to 450° C., and the composition of gas produced was monitored.

The concentration of gas produced was measured by a gas chromatograph (GC) downstream. The concentrations of $CH_4$, $CH_3Cl$, $CH_2Cl_2$, and $CHCl_3$ were measured by a flame ionization detector (FID), and the concentrations of $CH_4$, $N_2$, $O_2$, $CO_2$, and CO were measured by a thermal conductivity detector (TCD). In order to prevent the produced gas from being condensed, the produced gas may be heated up to 150° C.

The yield and selectivity related to the gas may be calculated by the following Mathematical Formulae 1 to 3. The correction factor (a) associated with the inlet and outlet nitrogen gas is calculated by the following Mathematical Formula 1.

$$\alpha = \frac{n(N_2)_{inlet}}{n(N_2)_{outlet}} \qquad \text{[Mathematical Formula 1]}$$

The $n(N_2)_{inlet}$ is the number of moles of a nitrogen gas flowing into the reactor, and the $n(N_2)_{outlet}$ is the number of moles of a nitrogen gas flowing out of the reactor.

The methane conversion (X, %) is calculated by the following Mathematical Formula 2.

$$X(CH_4) = \frac{n(CH_4)_{inlet} - \alpha \times n(CH_4)_{outlet}}{n(CH_4)_{inlet}} \times 100(\%) \qquad \text{[Mathematical Formula 2]}$$

The $n(CH_4)_{inlet}$ is the number of moles of a methane gas flowing into the reactor, and the $n(CH_4)_{outlet}$ is the number of moles of a methane gas flowing out of the reactor.

The selectivity (S) of the gas produced is calculated by the following Mathematical Formula 3.

$$S(j) = \frac{n(j)_{outlet}}{\Sigma n(j)_{outlet}} \times 100(\%) \qquad \text{[Mathematical Formula 3]}$$

The $n(j)_{outlet}$ is the number of moles of each produced gas flowing out of the reactor, and the $\Sigma n(j)_{outlet}$ is the total number of moles of the produced gases.

Meanwhile, during the experiments on the catalysts in the Examples and the Comparative Example, the process temperatures are the same as those in the following Tables 1 and 2.

Experimental Example 1: Experiment According to Types of Supported Material and Carrier Oxychlorination reactions of methane were performed by using the catalysts according to the Examples and the Comparative Examples. In this case, the yields of the respective products are shown in the following Tables 1 and 2 and FIG. 2.

TABLE 1

| Classification | Constitution/Type | | Example 1 | Example 2 | Comparative Example 1 | Comparative Example 2 | Comparative Example 3 | Comparative Example 4 |
|---|---|---|---|---|---|---|---|---|
| Type of catalyst | Supported material | | Cu(5), K(6), La(5) | Cu(7), K(2), La(2) | Cu(5), K(6), La(5) | Cu(7), K(2), La(2) | Cu(7), K(2), La(2)/ | Not supported |
| | Carrier | | $CeO_2$ | $CeO_2$ | $\gamma\text{-}Al_2O_3$ | $\gamma\text{-}Al_2O_3$ | CeZr | $CeO_2$ |
| Experimental results | Process temperature (° C.) | | 550 | 550 | 570 | Not performed | 510 | 550 |
| | Selectivity of Target product | $CH_3Cl$ | 15.1 | 14.8 | 10.5 | Not performed | 9.7 | 13.4 |
| | | $CH_2Cl_2$ | 6.8 | 6.8 | 2.9 | Not performed | 1.9 | 4.1 |
| | | $CHCl_3$ | 1.36 | 1.4 | 0.02 | Not performed | 0 | 0.07 |
| | Selectivity of byproduct | $CO_2$ | 0.4 | 0.4 | 4.4 | Not performed | 4.4 | 1.7 |
| | | CO | 0.2 | 0.5 | 2.4 | Not performed | 2.4 | 4.4 |

TABLE 2

| Classification | Constitution/Type | | Comparative Example 5 | Comparative Example 6 | Comparative Example 7 | Comparative Example 8 | Comparative Example 9 | Comparative Example 10 |
|---|---|---|---|---|---|---|---|---|
| Type of catalyst | Supported material | | Cu | K | L | Cu, K | Cu,La | Fe(5), K(6), La(5) |
| | Carrier | | $CeO_2$ | $CeO_2$ | $CeO_2$ | $CeO_2$ | $CeO_2$ | $CeO_2$ |
| Experimental results | Process temperature (° C.) | | 550 | 550 | 550 | 550 | 550 | 550 |
| | Selectivity of Target product | $CH_3Cl$ | 14.8 | 12.5 | 6.7 | 11.2 | 7.5 | 11.1 |
| | | $CH_2Cl_2$ | 5.2 | 3.5 | 2.1 | 3.5 | 1.9 | 3.7 |
| | | $CHCl_3$ | 0.12 | 0.08 | 0.33 | 0.26 | 0.24 | 0.6 |

TABLE 2-continued

| Classi-fication | Constitution/Type | | Comparative Example 5 | Comparative Example 6 | Comparative Example 7 | Comparative Example 8 | Comparative Example 9 | Comparative Example 10 |
|---|---|---|---|---|---|---|---|---|
| | Selectivity of byproduct | $CO_2$ | 3.4 | 1.9 | 0 | 0.2 | 0 | 0 |
| | | CO | 0.4 | 4.0 | 4.0 | 0.6 | 0.7 | 0.9 |

The cases where the same material was supported but the types of carriers were different were compared with one another. Specifically, it could be confirmed that in the case of the catalyst in which the type of carrier was $CeO_2$ (Examples 1 and 2), the selectivity of the chloro compound as the target product was high and the selectivity of carbon dioxide and carbon monoxide as the byproducts was low as compared to the case where the type of carrier was an aluminum oxide in the related art (Comparative Example 1: $\gamma$-$Al_2O_3$) or CeZr (Comparative Example 3).

The cases where the type of carrier was the same but different materials were supported were compared with one another. The catalyst according to Example 1 has an effect of lowering the production of the byproducts while increasing the selectivity of the target product ($CH_3Cl$, $CH_2Cl_2$, or $CHCl_3$) by using the catalyst material including all of copper-potassium-lanthanum. Specifically, it could be confirmed that in the case including copper as the catalyst material (Comparative Example 5), the selectivity of the product was excellent as compared to Comparative Examples 4, 6, and 7 including no copper. However, in the case of Comparative Example 5, there was a problem in that carbon dioxide and carbon monoxide as the byproducts were generated.

It could be confirmed that in the case where potassium was further included (Comparative Example 8) or lanthanum was further included (Comparative Example 9) in addition to copper as the catalyst material in order to solve the problem, the problem in that the byproducts were produced was solved to some degree, but the selectivity of the target product was decreased as compared to Comparative Example 4.

Accordingly, it was possible to minimize the production of the byproducts while maximizing the selectivity of the target product by including all of copper, potassium, and lanthanum as the catalyst materials in Example 1.

Meanwhile, it could be confirmed that in the case where iron was included instead of copper as the catalyst material (Comparative Example 10), a small amount of byproducts were produced, but the selectivity of the target product was low. The reason is because the activity of copper is better than the activity of iron.

Experimental Example 2: Experiment According to Process Temperature

The selectivity was calculated by using the catalyst according to Example 1 to measure the degree to which the gas was produced according to the temperature, and is shown in the following Table 3 and FIG. 3.

TABLE 3

| Process temperature (° C.) | Target product | | | Byproduct | |
|---|---|---|---|---|---|
| | $CH_3Cl$ | $CH_2Cl_2$ | $CHCl_3$ | $CO_2$ | CO |
| 450 | 6.7 | 1.3 | 0.09 | 0 | 0 |
| 480 | 9.2 | 2.6 | 0.28 | 0 | 0 |
| 510 | 12.1 | 4.4 | 0.66 | 0 | 0 |
| 530 | 14.0 | 5.7 | 1.00 | 0 | 0 |
| 550 | 15.1 | 6.8 | 1.36 | 0.4 | 0.2 |
| 570 | 15.2 | 6.7 | 1.26 | 0.3 | 0.9 |
| 590 | 14.4 | 6.8 | 1.42 | 0.3 | 1.3 |

It could be confirmed that when the process temperature was 550° C. or more, carbon dioxide and carbon monoxide as byproducts were partially produced, and the higher the process temperature was, the more byproducts were produced. The results as described above are due to the fact that when the process temperature was more than 530° C., the effect of temperature during the process was increased, and as a result, the produced $CH_3Cl$ additionally reacted or $CH_4$ was directly oxidized to produce large amounts of carbon dioxide and carbon monoxide as byproducts. In contrast, when the process temperature was 530° C. or less, it was possible to prevent carbon dioxide and carbon monoxide as byproducts from being produced by suppressing $CH_3Cl$ from additionally reacting, or suppressing $CH_4$ from being directly oxidized.

The results of the respective catalysts in Experimental Examples 1 and 2 are the same as those illustrated in FIGS. 2 to 4.

The invention claimed is:

1. A catalyst for an oxychlorination process of hydrocarbons, the catalyst comprising:
    a catalyst material comprising (a) copper, (b) a first co-catalyst comprising one or more selected from the group consisting of an alkali metal and an alkaline earth metal, and (c) a second co-catalyst comprising a lanthanide metal; and
    a carrier comprising cerium oxide.

2. The catalyst of claim 1, where the catalyst material is present in the catalyst in an amount of 5 wt % to 25 wt % based on a total weight of the catalyst.

3. The catalyst of claim 1, wherein an amount of the first co-catalyst and an amount of the second co-catalyst is the same as or different from each other, and the amount of the first co-catalyst and the amount of the second co-catalyst are each in an amount of 10 parts by weight to 2,000 parts by weight based on 100 parts by weight of copper.

4. The catalyst of claim 1, wherein the first co-catalyst comprises one or more selected from the group consisting of sodium, lithium, potassium, magnesium, and calcium.

5. The catalyst of claim 1, wherein the second co-catalyst further comprises one or more selected from the group consisting of yttria and a rare earth element.

6. The catalyst of claim 1, wherein the carrier has a specific surface area of 50 m²/g to 250 m²/g.

7. The catalyst of claim 1, wherein cerium oxide is present in the carrier in an amount of 80 wt % or more based upon a total 100 wt % of the carrier.

8. The catalyst of claim 1, wherein the catalyst is in the form of particles having a diameter of 0.1 mm to 1.0 mm.

9. A method for preparing the catalyst for an oxychlorination process of hydrocarbons according to claim 1, the method comprising:
   preparing a carrier comprising cerium oxide; and
   supporting an active material comprising copper, a first co-catalyst, and a second co-catalyst on the carrier.

10. A method for preparing an oxychlorination compound of hydrocarbons, comprising:
    performing an oxychlorination reaction of hydrocarbons in the presence of the catalyst according to claim 1.

11. The method of claim 10, wherein the method is performed under a process temperature of 450° C. to 550° C., a pressure of 0.5 atm to 3 atm, and a space velocity of 2,000 $h^{-1}$ to 20,000 $h^{-1}$.

12. The method of claim 10, wherein the method is performed in a packed bed reactor, a fluidized bed reactor, or a circulating fluidized bed reactor.

13. The catalyst of claim 1, wherein cerium oxide is present in the carrier in an amount of 90 wt % or more based upon a total 100 wt % of the carrier.

14. The catalyst of claim 1, wherein cerium oxide is present in the carrier in an amount of 99 wt % or more based upon a total 100 wt % of the carrier.

15. The catalyst of claim 1, wherein the carrier consists of cerium oxide.

* * * * *